US011497671B2

(12) United States Patent
Lakany et al.

(10) Patent No.: US 11,497,671 B2
(45) Date of Patent: Nov. 15, 2022

(54) APPARATUS FOR THE REHABILITATION, ASSISTANCE AND/OR AUGMENTATION OF ARM STRENGTH IN A USER

(71) Applicant: University of Strathclyde, Glasgow (GB)

(72) Inventors: Heba Lakany, Glasgow (GB); Lijo Varughese Chacko, Glasgow (GB)

(73) Assignee: University of Strathclyde, Glasgow (GB)

( * ) Notice: Subject to any disclaimer, the term of this patent is extended or adjusted under 35 U.S.C. 154(b) by 272 days.

(21) Appl. No.: 16/652,520

(22) PCT Filed: Oct. 2, 2018

(86) PCT No.: PCT/GB2018/052810
§ 371 (c)(1),
(2) Date: Mar. 31, 2020

(87) PCT Pub. No.: WO2019/069069
PCT Pub. Date: Apr. 11, 2019

(65) Prior Publication Data
US 2020/0281796 A1    Sep. 10, 2020

(30) Foreign Application Priority Data

Oct. 2, 2017 (GB) .................................. 1716043

(51) Int. Cl.
*A61H 1/02* (2006.01)
*A61F 5/01* (2006.01)

(52) U.S. Cl.
CPC .......... *A61H 1/0281* (2013.01); *A61F 5/0118* (2013.01); *A61H 1/0277* (2013.01);
(Continued)

(58) Field of Classification Search
CPC .. A61H 1/0274; A61H 1/0277; A61H 1/0281; A61H 1/0285
See application file for complete search history.

(56) References Cited

U.S. PATENT DOCUMENTS 4,180,870 A * 1/1980 Radulovic ............... A61F 5/013
601/33
6,113,562 A 9/2000 Bonutti et al.
(Continued)

FOREIGN PATENT DOCUMENTS

| CN | 103519966 | 1/2014 |
| CN | 105597280 | 5/2016 |

(Continued)

OTHER PUBLICATIONS

Zhang et al. "Robotic arm for unsupervised stroke rehabilitation: A pilot study using PID controller", IEEE Xplore, May 30, 2013. (Year: 2013).*

(Continued)

*Primary Examiner* — Samchuan C Yao
*Assistant Examiner* — Savannah L Gabriel
(74) *Attorney, Agent, or Firm* — Myers Bigel, P.A.

(57) ABSTRACT

An apparatus (10) for the rehabilitation, assistance and/or augmentation of arm strength in a user (U) comprises a support arrangement (12) for supporting the apparatus (10) on the user (U), a linkage arrangement (14) coupled to the support arrangement (12) and for coupling to an arm (A) of the user (U), and an actuation arrangement (16) for operating the linkage arrangement (14) and thereby manipulating the user's arm (A) in response to a user input signal.

19 Claims, 10 Drawing Sheets

(52) U.S. Cl.
CPC ............... *A61F 2005/0155* (2013.01); *A61F 2005/0179* (2013.01); *A61F 2005/0188* (2013.01); *A61H 2201/1215* (2013.01); *A61H 2201/1454* (2013.01); *A61H 2201/165* (2013.01); *A61H 2201/1635* (2013.01); *A61H 2201/5007* (2013.01); *A61H 2201/5061* (2013.01); *A61H 2201/5071* (2013.01); *A61H 2201/5084* (2013.01)

(56) References Cited

U.S. PATENT DOCUMENTS

| | | | |
|---|---|---|---|
| 6,114,296 | A | 9/2000 | Schulein et al. |
| 6,265,197 | B1 | 7/2001 | Bisgåard-Frantzen et al. |
| 6,599,263 | B1 | 7/2003 | Bonutti et al. |
| 6,921,656 | B1 | 7/2005 | Koyama et al. |
| 7,375,197 | B2 | 5/2008 | Adney et al. |
| 7,695,947 | B2 | 4/2010 | Sung |
| 7,785,854 | B2 | 8/2010 | St-Pierre et al. |
| 7,862,524 | B2 * | 1/2011 | Carignan ............... B25J 17/025 601/5 |
| 8,246,559 | B2 | 8/2012 | Hoffman et al. |
| 8,945,903 | B2 | 2/2015 | Baidyaroy et al. |
| 9,080,163 | B2 | 7/2015 | Mitchell et al. |
| 2010/0063601 | A1* | 3/2010 | Sankai ................... B25J 9/0006 623/25 |
| 2012/0165158 | A1 | 6/2012 | Ren et al. |
| 2015/0173992 | A1 | 6/2015 | Wang |
| 2015/0272807 | A1 | 10/2015 | Gupta et al. |
| 2016/0051388 | A1* | 2/2016 | Goldfarb ................ A61F 5/013 602/16 |
| 2016/0206497 | A1* | 7/2016 | Deshpande ............... A61F 2/76 |
| 2017/0022486 | A1 | 1/2017 | Yao et al. |
| 2017/0055883 | A1 | 3/2017 | Lee et al. |
| 2017/0224517 | A1* | 8/2017 | Doyle .................... B25J 9/0006 |
| 2017/0296418 | A1* | 10/2017 | Lee ....................... A61H 1/0281 |
| 2018/0194000 | A1* | 7/2018 | Smith ..................... B25J 9/148 |
| 2018/0235829 | A1* | 8/2018 | Ryu .................. A63B 21/00181 |

FOREIGN PATENT DOCUMENTS

| | | | | |
|---|---|---|---|---|
| CN | 105963103 | | 9/2016 | |
| CN | 107374907 | | 11/2017 | |
| EP | 0585285 | | 8/1998 | |
| EP | 1065277 | | 3/2001 | |
| EP | 1184460 | | 6/2002 | |
| EP | 1364755 | A1 * | 11/2003 | ........... A61H 1/0274 |
| EP | 0937138 | | 4/2006 | |
| EP | 1571207 | | 12/2008 | |
| EP | 2083074 | | 7/2009 | |
| EP | 1654355 | | 4/2010 | |
| EP | 2447361 | | 5/2012 | |
| EP | 2475338 | | 7/2016 | |
| EP | 3156193 | | 4/2017 | |
| EP | 3184633 | | 6/2017 | |
| EP | 2070492 | | 8/2017 | |
| ES | 2370895 | | 12/2011 | |
| FR | 299381 | * | 1/2014 | ........... B25J 9/0006 |
| GB | 2444679 | | 6/2008 | |
| JP | 2009268839 | | 11/2009 | |
| JP | 2017024086 | | 2/2017 | |
| WO | 2010092089 | | 8/2010 | |
| WO | 2010095619 | | 8/2010 | |
| WO | 2015099858 | | 7/2015 | |
| WO | 2015168788 | | 11/2015 | |
| WO | 2016166588 | | 10/2016 | |
| WO | 2017167349 | | 10/2017 | |
| WO | WO-20180943448 | * | 5/2018 | ........... A61H 1/0285 |

OTHER PUBLICATIONS

"The 5 things you need to know about Cone Drive Harmonic Solutions", Cone Drive. Aug. 5, 2016. (Year: 2016).*

Benitez et al. "Exoskeleton Technology in Rehabilitation: Towards an EMG-Based Orthosis System for Upper Limb Neuromotor Rehabilitation" Journal of Robotics, 2013(610589):1-13 (2103).

Chen et al. "Design of a 6-DOF upper limb rehabilitation exoskeleton with parallel actuated joints" Bio-Medical Materials and Engineering, 24:2527-2535 (2014).

Garrido et al. "Modular design and control of an upper limb exoskeleton" Journal of Mechanical Science and Technology, 30(5):2265-2271 (2016).

Harmonic Drive AG "Engineering Data: SHD-2SH Units" Product description, www.harmonicdrive.de/2080 (51 pages) (2014).

International Preliminary Report on Patentability corresponding to International Patent Application No. PCT/GB2018/052810 (9 pages) (dated Apr. 16, 2020).

Maxon Motor Control "ESCON 70/10 Servo Controller, P/N 422969" Hardware Reference (40 pages) (Edition Nov. 2015).

Merrell et al. "Results of Nerve Transfer Techniques for Restoration of Shoulder and Elbow Function in the Context of a Meta-analysis of the English Literature" Journal of Hand Surgery, 26A:303-314 (2001).

Nef et al. "ARMin III—arm therapy exoskeleton with an ergonomic shoulder actuation" Applied Bionics and Biomechanics, 6(2):127-142 (2009).

Perry et al. "Upper-Limb Powered Exoskeieton Design" IEEE/ASME Transactions on Mechatronics, 12(4):408-417 (2007).

Peternal et al. "Adaptive Control of Exoskeleton Robots for Periodic Assistive Behaviours Based on EMG Feedback Minimisation" PLoS ONE, 11(2):e0148942 (2016).

Sanchez et al. "A Pneumatic Robot for Re-Training Arm Movement after Stroke: Rationale and Mechanical Design" Proceedings of the 2005 IEEE 9th International Conference on Rehabilitation Robotics, Jun. 28-Jul. 1, 2005, Chicago, IL, USA, pp. 500-504 (2005).

Senalp et al. "Static, dynamic and fatigue behaviour of newly designed stem shapes for hip prosthesis using finite element analysis" Materials & Design, 28:1577-1583 (2007).

Smania et al. "Rehabilitation of brachial plexus injuries in adults and children" European Journal of Physical and Rehabilitation Medicine, 48(3):483-506 (2012).

Sugar et al., "Design and Control of RUPERT: A Device for Robotic Upper Extremity Repetitive Therapy" IEEE Transactions o Neural Systems and Rehabilitation Engineering, 15(3):336-346 (2007).

Taghirad et al. "Modeling and Parameter Identification of Harmonic Drive Systems" Journal of Dynamic Systems, Measurement, and Control, 120:439-444 (1998).

Texas Instruments "C2000™ Digital Controller Library" User's Guide (61 pages) (Jul. 2015).

International Search Report and the Written Opinion of the International Searching Authority corresponding to International Patent Application No. PCT/GB2018/052810 (12 pages) (dated Dec. 12, 2018).

Search Report under Section 17(5) corresponding to GB Application No. 1716043.3 (2 pages) (dated Feb. 23, 2018).

* cited by examiner

APPARATUS FOR THE REHABILITATION, ASSISTANCE AND/OR AUGMENTATION OF ARM STRENGTH IN A USER

FIELD

The present invention relates to an apparatus for the rehabilitation, assistance and/or augmentation of arm strength in a user.

BACKGROUND

Partial paralysis affects a significant number of people around the World, whether as result of an inherited condition or due to an injury. In some instances, partial paralysis may be the result of a stroke. In other instances, partial paralysis may be result of an injury to the brachial plexus nerve—a network of neurons originating from the spinal cord which carries the motor and sensory information between the brain and the upper limbs.

Brachial Plexus Injury (BPI) may for example be caused by an inflammatory disease, by a tumour impinging on the brain, during childbirth, or by traumatic injury and typically leads to functional impairment and disability to one or more of the upper limbs.

Direct effects of BPI are muscle atrophy, pain and somatosensory deficit. BPI can also affect the patients psychologically.

BPI patients require early and prolonged treatment. Surgical reinnervation is often necessary to repair an injury caused due to muscle denervation.

However, physical therapy is required before and after the surgical reinnervation in order to prevent the development of muscular contracture, joint stiffness and secondary deformities in the affected arm, since denervated muscle can develop atrophy within weeks.

Currently, physical therapy is provided for BPI patients immediately on their diagnosis to prevent the development of muscle contracture, joint stiffness and secondary deformities, with muscle stretching the primary task given by therapists to avoid muscular atrophy.

Orthosis devices are used in physical therapy and include braces, splints, or other external devices which function to support the limbs or spine of a user or to prevent and assist relative movement.

More recently, the emergence of robotic technology has been introduced to assist users in the rehabilitation of stroke patients.

However, there are a number of drawbacks with conventional equipment.

For example, although current systems are capable of providing sufficient power to anatomical joints for performing various upper arm movements, these systems are bulky and not portable. Hence, these devices are limited to laboratory or clinical environments and not capable of providing physical therapy for BPI patients while they are at home.

Moreover, conventional robotic equipment requires a muscle activity signal to control and operate. However, in the case of users with complete paralysis of the given limb, such a muscle activity signal is not present.

SUMMARY

According to a first aspect, there is provided a wearable orthosis apparatus for use in the rehabilitation, assistance and/or augmentation of arm strength in a user, comprising:

a support arrangement for supporting the apparatus on the user, such that the apparatus can be carried by the user;

a linkage arrangement coupled to the support arrangement and configured for coupling to an arm of a user; and an actuation arrangement coupled to the linkage arrangement and configured to move the linkage arrangement and thereby manipulate the user's arm in response to a user input signal.

The apparatus may comprise or take the form of an exoskeleton.

Beneficially, embodiments of the apparatus provide a lightweight and portable device suitable for being carried by the user, facilitating rehabilitation of the arm for people with partial paralysis in a home setting. In the case of Brachial Plexus Injury (BPI), embodiments of the apparatus are capable of providing an active force to perform flexion and extension of the elbow joint, thereby reducing the occurrence of muscle contracture and joint stiffness while also functioning to stabilise the arm in a similar manner to a conventional splint used in rehabilitation process for BPI patients. Embodiments of the apparatus may alternatively be used for assistance of people with arm weakness, such as older people, to perform activities of daily life such as carrying and/or lifting; and/or as an augmentative device to increase the arm capability in industrial or military environments, thereby reducing metabolic cost and/or fatigue.

The user input signal may comprise a signal resulting from a force applied to the linkage arrangement by the user.

The user input signal may be generated by a sensor arrangement.

The sensor arrangement may comprise a sensor.

The sensor may comprise an accelerometer.

The user input signal may comprise a signal from a switch or other input device operated by the user, in particular but not exclusively using the user's other arm.

As described above, the apparatus comprises a support arrangement for supporting the apparatus on the user.

Beneficially, the support arrangement permits the apparatus to be carried by the user, in contrast to conventional fixed station rehabilitation equipment. Embodiments of the present invention thus permit rehabilitation therapies to be carried out by the user themselves in a home environment.

The support arrangement may comprise a back plate.

The back plate may support the mass of the linkage arrangement and the actuation arrangement on the user.

Users with reduced or no feeling in their arm are known to be adversely affected by postural balance issues due at least in part to the lack of feedback from the affected arm, balance issues which can be exacerbated by any unbalanced load on one side of the user's body. Beneficially, the back plate distributes the weight of the apparatus across the back of the user, such that the user will not feel weight a significant unbalanced load on one side of their body due to the asymmetric location of the apparatus on one arm.

The back plate may be constructed from any suitable material.

In particular embodiments, the back plate is constructed from a carbon fibre composite material.

Beneficially, the provision of a back plate which is constructed from a carbon fibre composite material reduces the weight to be carried to be user while being sufficiently strong to carry the mass of the other components of the apparatus, including amongst other things the linkage arrangement and the actuation arrangement.

The support arrangement may comprise one or more strap.

The support arrangement may comprise one or more shoulder strap.

In particular embodiments, the support arrangement comprises two shoulder straps.

The shoulder strap(s) may be coupled to the back plate.

The or each shoulder strap may be disposed through a slot in the back plate.

The shoulder strap, or in embodiments comprising a plurality of shoulder straps at least one of the shoulder straps, may be adjustable. For example, a slide adjuster or other suitable adjuster may be provided to permit the shoulder strap to be adjusted. Beneficially, the provision of adjustable shoulder straps permits the apparatus to be adapted to the user's anthropometry.

A clasp may be provided to secure the shoulder straps together.

The support arrangement may comprise one or more waist strap.

In particular embodiments, the support arrangement comprises two waist straps.

The waist strap, or in embodiments comprising a plurality of waist straps at least one of the waist straps, may be adjustable. For example, a slide adjuster or other suitable adjuster may be provided to permit the shoulder strap to be adjusted.

Beneficially, the provision of adjustable waist straps permits the apparatus to be adapted to the user's anthropometry.

A clasp may be provided to secure the waist straps together.

The support arrangement may take other forms. For example, at least part of the support arrangement may be integrally formed with a garment, such as a jacket, suitable for being worn by the user.

As described above, the linkage arrangement is coupled to the support arrangement and configured for coupling to an arm of the user.

The linkage arrangement may comprise a first linkage element.

The first linkage element may take the form of a shoulder rod.

The first linkage element may be coupled to the back plate.

The first linkage element may be coupled to the back plate by a coupler.

The first linkage element may be coupled to the back plate such that the first linkage element extends vertically or substantially vertically relative to the user.

The first linkage element may be rotatable about a vertical or substantially vertical axis relative to the user.

In use, rotation of the first linkage element relative to the vertical or substantially vertical axis may provide a first degree of freedom of the apparatus.

The first linkage element may be rotatably coupled at a first end to the coupler and at a second end to a coupler block, such that the shoulder rod is rotatable about the vertical or substantially vertical axis relative to the user.

The first linkage element may be rotatably coupled at the first end to the coupler by a bearing, e.g., a roller bearing, and at the second end to the coupler block by a bearing, e.g., a roller bearing.

The first linkage element may be constructed from any suitable material.

In particular embodiments, the first linkage element may be constructed from steel, more particularly but not exclusively structural steel.

The linkage arrangement may comprise a second linkage element.

The second linkage element may take the form of angled shoulder rod.

The second linkage element may extend horizontally or substantially horizontally relative to the user.

The second linkage element may be rotatable about a horizontal or substantially horizontal axis relative to the user.

The second linkage element may be rotatably coupled to the coupler block.

The second linkage element may be rotatably coupled at a first, proximal, end to the coupler block and at a second, distal, end to the third linkage element.

The second linkage element may be rotatably coupled at the first, proximal, end to the coupler block by a bearing, e.g., a roller bearing, and at the second, distal, end to the third linkage element by a bearing, e.g., a roller bearing.

In use, rotation of the second linkage element may provide a second degree of freedom of the apparatus.

The second linkage arrangement may be constructed from any suitable material.

In particular embodiments, the second linkage arrangement is constructed from aluminium alloy.

The linkage arrangement may comprise a third linkage element.

The third linkage element may take the form of a shoulder link.

The third linkage element may be coupled at a first, proximal, end to the distal end of the second linkage element and at a second, distal, end to the fourth linkage element.

The third linkage element may be curved. The third linkage element may be curved such that, in use, the third linkage element extends in an anterior direction (towards the user's front) such that the distal end of the third linkage element is disposed above, and rests on, the user's clavicle.

The third linkage element may be configured to pivot about a third axis to provide a third degree of freedom of the apparatus.

The third linkage element may comprise a unitary component. The third linkage element may be custom built to match the user's anthropometry.

Alternatively, the third linkage element may be adjustable to match the user's anthropometry. For example, the third linkage element may comprise a plurality of components coupled by a slider coupling or in a telescopic relationship.

The third linkage arrangement may be constructed from any suitable material.

In particular embodiments, the third linkage arrangement is constructed from aluminium alloy.

The linkage arrangement may comprise a fourth linkage element.

The fourth linkage element may take the form of an upper arm member.

The fourth linkage element may be configured to pivot about a fourth axis to provide a fourth degree of freedom of the apparatus.

The fourth linkage element may be coupled at a first, upper, end to the third linkage element and at a second, lower, end to the actuator arrangement of the apparatus.

The fourth linkage element may be coupled at the first, upper, end to the third linkage element by a bearing, e.g. a roller bearing, and at the second, lower, end to the actuator arrangement of the apparatus by a bearing, e.g. a roller bearing.

The fourth linkage element may be adjustable to match the user's anthropometry.

The fourth linkage element may comprise a first upper arm element and a second upper arm element.

The first upper arm element and the second upper arm element may be coupled together by a slider coupling.

The first upper arm element and the second upper arm element may alternatively be arranged in a telescopic relationship.

Alternatively, the third linkage element may comprise a unitary component. The third linkage element may be custom built to match the user's anthropometry, such as by additive manufacture or other suitable method of manufacture.

The fourth linkage arrangement may be constructed from any suitable material.

In particular embodiments, the fourth linkage arrangement is constructed from aluminium alloy.

The linkage arrangement may comprise a fifth linkage element.

The fifth linkage element may take the form of lower arm member.

The fifth linkage element may be coupled at a first, upper, end to the actuator arrangement of the apparatus.

The fifth linkage element may be adjustable to match the user's anthropometry. The fifth linkage element may comprise a first lower arm element and a second lower arm element.

The first lower arm element and the second lower arm element may be coupled together by a slider coupling.

The first lower arm element and the second lower arm element may alternatively be arranged in a telescopic relationship.

Alternatively, the fifth linkage element may comprise a unitary component. The fifth linkage element may be custom built to match the user's anthropometry, such as by additive manufacture or other suitable method of manufacture.

The fifth linkage arrangement may be constructed from any suitable material.

In particular embodiments, the fifth linkage arrangement is constructed from aluminium alloy.

The linkage arrangement may comprise a shoulder joint assembly configured to provide three degrees of freedom of movement.

The shoulder joint assembly may be passive.

The linkage arrangement may comprise an arm assembly configured to provide two degrees of freedom of movement.

The arm assembly may be active.

Beneficially, embodiments of the apparatus are capable of five degrees of freedom of movement, the first linkage element, second linkage element, and third linkage element forming a shoulder joint assembly of the apparatus providing three degrees of freedom of movement while the fourth linkage element and fifth linkage element form an arm assembly of the apparatus providing two degrees of freedom of movement.

In particular embodiments, the shoulder joint assembly is passive, that is it is not directly driven by the actuation arrangement and the elbow joint defined by the arm assembly is active, that is it is directly driven by the actuation arrangement.

In particular embodiments, one or more spring element or other resilient element may be provided to stabilise free movement of the shoulder joint assembly.

The one or more spring element or other resilient element may form part of the support arrangement of the apparatus.

Beneficially, the provision of one or more spring element or other resilient element may improve the stability of the apparatus and may support the position of the linkage arrangement.

The tension and/or length of the one or more spring element or other resilient element spring may be selected according to the user's anthropometry.

The linkage arrangement may comprise a cuff.

The cuff may be configured for coupling the apparatus to the user's lower arm. In use, force generated by the actuator arrangement is transferred to the arm through the cuff, delivering the required assistive torque to the users elbow joint.

The cuff may be coupled to, or form part of, the lower arm member.

One or more adjustable strap may be provided to secure the lower arm to the cuff.

At least part of the sensor arrangement may be disposed in, or mounted on, the cuff.

For example, the sensor of the sensor arrangement may be disposed in, or mounted on, the cuff.

As described above, the actuation arrangement is coupled to the linkage arrangement and configured to operate the linkage arrangement and thereby manipulate the arm in response to the user input signal.

In use, the actuation arrangement may be used for power assisted rehabilitation of the arm for people with paralysis, for example as a result of a stroke or injury as part of their treatment within a clinic, medical establishment or in a home setting. The apparatus may be used for assistance of people with arm weakness, such as older people, to perform activities of daily life such as carrying and/or lifting. The apparatus may be used as an augmentative device to increase the arm capability in industrial or military environments, thereby reducing metabolic cost and/or fatigue.

The actuation arrangement may comprise a rotary drive.

The rotary drive may comprise a motor.

The motor may comprise an electric motor.

The motor may comprise a direct current (DC) electric motor.

In particular embodiments, the motor comprises a brushless DC electric motor (a "BLDC" motor).

Beneficially, the use of a BLDC motor provides a high power-to-weight ratio while also providing a sufficiently fast response time to meet the user need for responsiveness.

The actuation arrangement may comprise a gear arrangement.

The gear arrangement may be interposed between the rotary drive and the linkage arrangement.

The gear arrangement may comprise a strain wave gear drive.

In particular embodiments, the gear arrangement comprises a harmonic Drive®.

In particular embodiments, the gear arrangement may be configured to provide a gear reduction ratio of 1:100. However, the gear arrangement may be configured to provide any suitable gear reduction ratio.

Beneficially, the provision of a strain wave gear drive provides a gear drive which is compact, has low backlash, high gear reduction ratio and low weight for the given gear ratio.

The actuation arrangement may comprise a coupler for attaching the non-moving parts of the rotary drive and the gear arrangement. The coupler may be configured to attach a housing of the rotary drive to a housing of the gear arrangement. The coupler may, for example, comprise an attachment plate.

The actuation arrangement may comprise a coupler for coupling the moving parts of the rotary drive and the gear arrangement. The coupler may be configured to attach a drive shaft of the rotary drive to an output shaft of the gear arrangement. In embodiments where the gear arrangement comprises a strain wave gear drive, the coupler may be configured to attach the drive shaft of the rotary drive to the flex spline of the strain wave gear drive.

The actuation arrangement may comprise a sensor arrangement comprising a sensor configured to sense the user input signal applied to the apparatus by the user.

The sensor may be configured to sense a mechanical force applied to the cuff by the user.

The sensor may comprise an accelerometer.

The actuation arrangement may comprise a controller configured to actuate an actuation arrangement of the apparatus in response to the user input signal to operate the linkage arrangement, and thereby manipulate the user's arm in response to the user input signal.

The controller may comprise an encoder.

The controller may comprise a rotary encoder.

In particular embodiments, the controller may comprise a magnetic rotary encoder.

Beneficially, the magnetic rotary encoder provides high accuracy and low footprint.

The encoder may be incorporated into an encoder housing.

The encoder may be configured to measure the position of the linkage arrangement.

The controller may comprise a magnet.

The apparatus may comprise, or may be operatively associated with, a position controller. In use, the position controller may be configured to control the position of the output shaft of the gear arrangement.

In particular embodiments, the position controller comprises a software based PID (Proportional Integral Derivative) position controller.

A digital PID controller may be implemented in a 32-bitARM microcontroller unit (MCU).

The controller may comprise anti-windup and/or output saturation limit features.

The controller may comprise a derivative filter. Beneficially, the provision of a derivative filter mitigates or reduces noise.

The MCU may comprise a 12-bit analogue to digital converter (ADC).

The MCU may comprise a 10-bit digital-to-analogue converter (DAC) for communicating with external devices.

In use, the output from the magnetic encoder—an analogue voltage—is digitised by the ADC in the MCU and then converted into degrees based on a calibration curve. The output of the controller may then be given to the ESCON controller via the DACport in the MCU. The control algorithm is implemented in a timer interrupt to run at a sampling frequency of 1000 Hz.

The position controller may be configured to operate as a cascading control system consisting of an inner and outer control loop. The inner loop may be implemented in the ESCON board and corresponds to a motor speed controller that maintains the required speed of the rotary drive.

The outer loop may monitor the current shaft position of the output shaft of the gear arrangement.

Based on the differences between the reference position and current position, the controller may generate a corresponding voltage which is sent as an input to the speed controller via the DAC port in MCU.

On receiving the input from the DAC, the speed controller may then control the speed and direction of the rotary drive.

When there is no error between the reference position and feedback position, the output from the PID controller becomes zero and thus brings the motor to an idle position.

The apparatus may comprise an electronics enclosure.

The electronics enclosure may be disposed on the back plate.

The electronics enclosure may house the control arrangement for the apparatus.

The apparatus may comprise an onboard power supply.

The onboard power supply may comprise a battery.

The onboard power supply may comprise a rechargeable battery pack.

The onboard power supply may be supported by the support arrangement.

The onboard power supply may be disposed in the electronics enclosure.

According to a second aspect, there is provided an actuation arrangement for a wearable orthosis apparatus for use in the rehabilitation, assistance and/or augmentation of arm strength in a user, the actuation arrangement comprising:

a sensor arrangement comprising a sensor configured to sense a user input signal applied to the apparatus by a user, the user input signal comprising a pressure force applied to a linkage arrangement of wearable orthosis apparatus; and a controller configured to actuate an actuation arrangement of the apparatus in response to the user input signal to operate a linkage arrangement, and thereby manipulate the user's arm in response to the user input signal.

A third aspect relates to use of the apparatus to rehabilitate arm strength in a user.

In use, the apparatus may be used for power assisted rehabilitation of the arm for people with paralysis, for example as a result of a stroke or injury as part of their treatment within a clinic, medical establishment or in a home setting.

A fourth aspect relates to use of the apparatus to rehabilitate, assist and/or augment arm strength in a user.

In use, the apparatus may be used for assistance of people with arm weakness, such as older people, to perform activities of daily life such as carrying and/or lifting. The apparatus may be used as an augmentative device to increase the arm capability in industrial or military environments, thereby reducing metabolic cost and/or fatigue.

In particular embodiments, the apparatus further comprises a movement limiter arrangement.

The movement limiter arrangement may comprise one or more safety stop.

The movement limiter arrangement may be configured to limit movement of the elbow joint to the natural limit of movement of the user's elbow, e.g. 0 to 130 degrees.

Alternatively or additionally, the movement limiter arrangement may comprise a software algorithm. The software algorithm may be configured to check the range of motion continuously. If the range of motion exceeds the set limits, the software may be configured to turn off the power to the rotary drive.

The apparatus may comprise a safety switch, e.g. an electrical switch, provided to the user to shut off the power to the rotary drive in case of an emergency.

Beneficially, the movement limiter arrangement and the switch ensure the safety of the apparatus for the user.

It should be understood that the features defined above or described below may be utilised, either alone or in combination with any other defined feature.

BRIEF DESCRIPTION OF THE DRAWINGS

These and other aspects will now be described with reference to the accompanying drawings, in which.

DETAILED DESCRIPTION OF THE DRAWINGS

Figure 1:
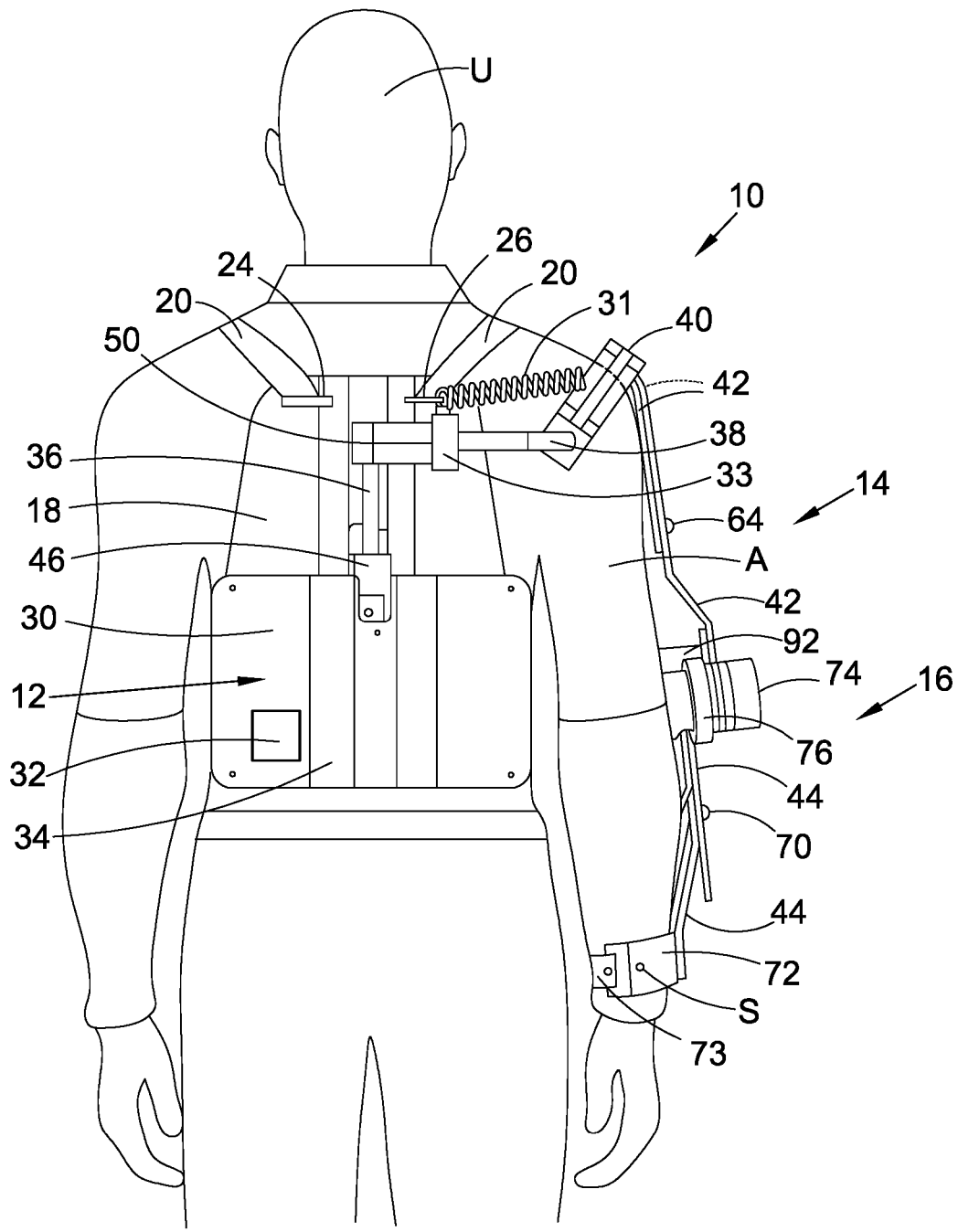
FIG. 1 shows a wearable orthosis apparatus according to a first embodiment of the present invention.
Figure 2:
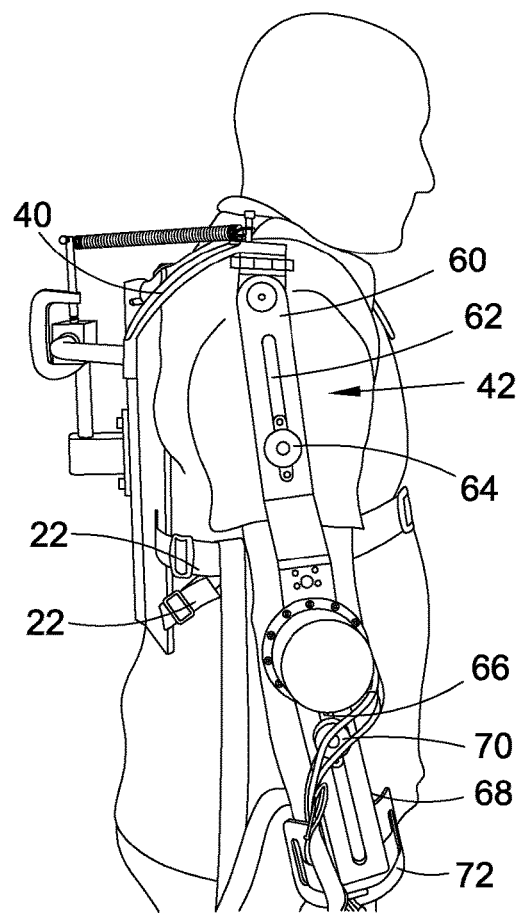
FIG. 2 shows a perspective view of the wearable orthosis apparatus shown in FIG. 1.
Figure 3:
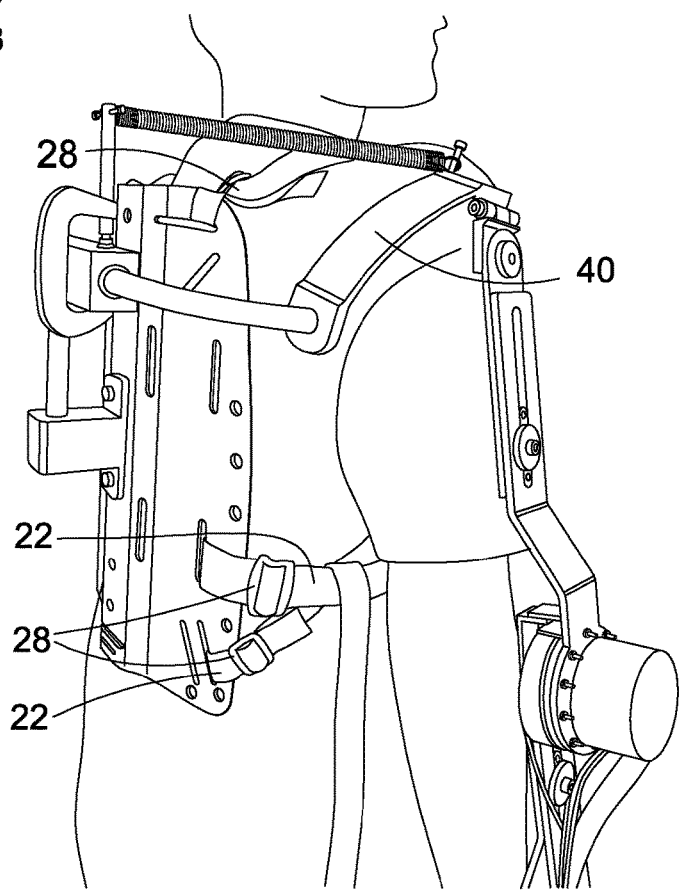
FIG. 3 shows another perspective view of the wearable orthosis apparatus shown in FIG. 1.

Referring first to FIGS. 1, 2 and 3 of the accompanying drawings, there is shown a wearable orthosis apparatus 10 for use in the rehabilitation, assistance and/or augmentation of arm strength in a user U.

As shown in FIG. 1, the apparatus 10 comprises a support arrangement 12 for supporting the apparatus 10 on the user U, a linkage arrangement 14 coupled to the support arrangement 12 and for coupling to an arm A of the user U, and an actuation arrangement 16 for operating the linkage arrangement 14 and thereby manipulating the user's arm A in response to a user input signal.

In the illustrated embodiment, the support arrangement 12 comprises a back plate 18, shoulder straps 20, and waist straps 22 (shown most clearly in FIGS. 2 and 3). The shoulder straps 20 and waist straps 22 extend through slots 24, 26 in the back plate 18 and comprise slide adjusters 28 or other suitable adjusters, to permit the support arrangement 12 to be adapted to the user's U anthropometry.

While in the illustrated embodiment, shoulder straps 20 and waist straps 22 are provided, it will be recognised that the support arrangement 12 may take a number of different forms. For example, some embodiments may be provided without waist straps. At least part of the support arrangement 12 may alternatively be integrally formed with a garment, such as a jacket, suitable for being worn by the user U.

An electronics enclosure 30 is disposed on the back plate 18. The electronics enclosure 30 houses a controller 32 for the apparatus 10. An onboard power supply in the form of a battery pack 34 is disposed in the electronics enclosure 30.

The back plate 18 supports the mass of the linkage arrangement 14 and the actuation arrangement 16.

One or more spring element or other resilient element 31 may be provided to stabilise free movement of the shoulder joint assembly. In the illustrated embodiment, the spring element 31 is attached via spring attachment 33.

Users with reduced or no feeling in their arm are known to be adversely affected by postural balance issues due at least in part to the lack of feedback from the affected arm, balance issues which can be exacerbated by any unbalanced load on one side of the user's body. Beneficially, the back plate 18 distributes the weight of the apparatus 10 across the back of the user U, such that the user U will not feel weight a significant unbalanced load on one side of their body due to the asymmetric location of the apparatus 10 on one arm.

In the illustrated embodiment, the back plate 18 is constructed from a carbon fibre composite material, providing a back plate 18 which is lightweight while being strong enough to carry the mass of the linkage arrangement 14, the actuation arrangement 16, the electronics enclosure 30 and the battery pack 34.

As described above, the back plate 18 provides mounting for the linkage arrangement 14.

Figure 4:
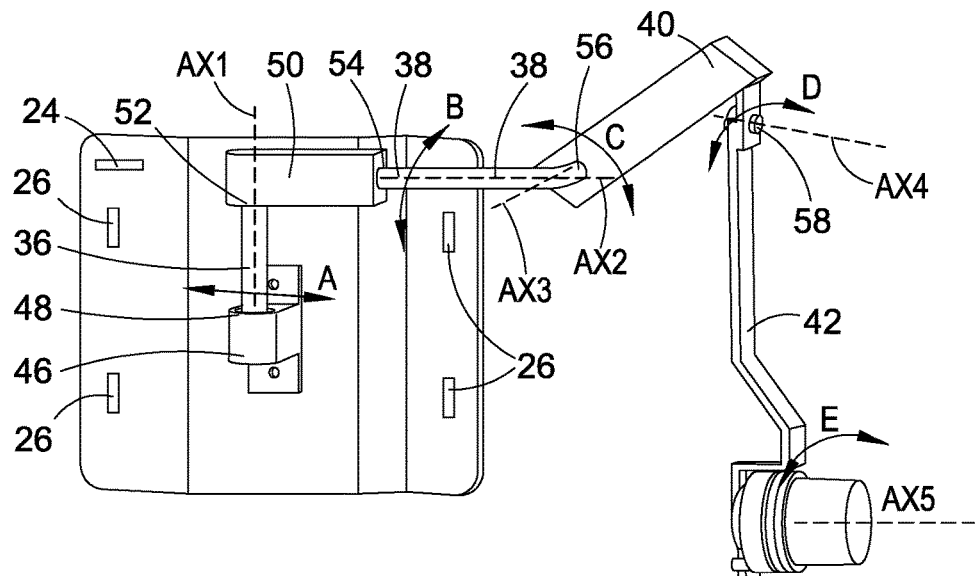
FIG. 4 shows a front perspective view of the wearable orthosis apparatus shown in FIGS. 1 to 3.
Figure 5:
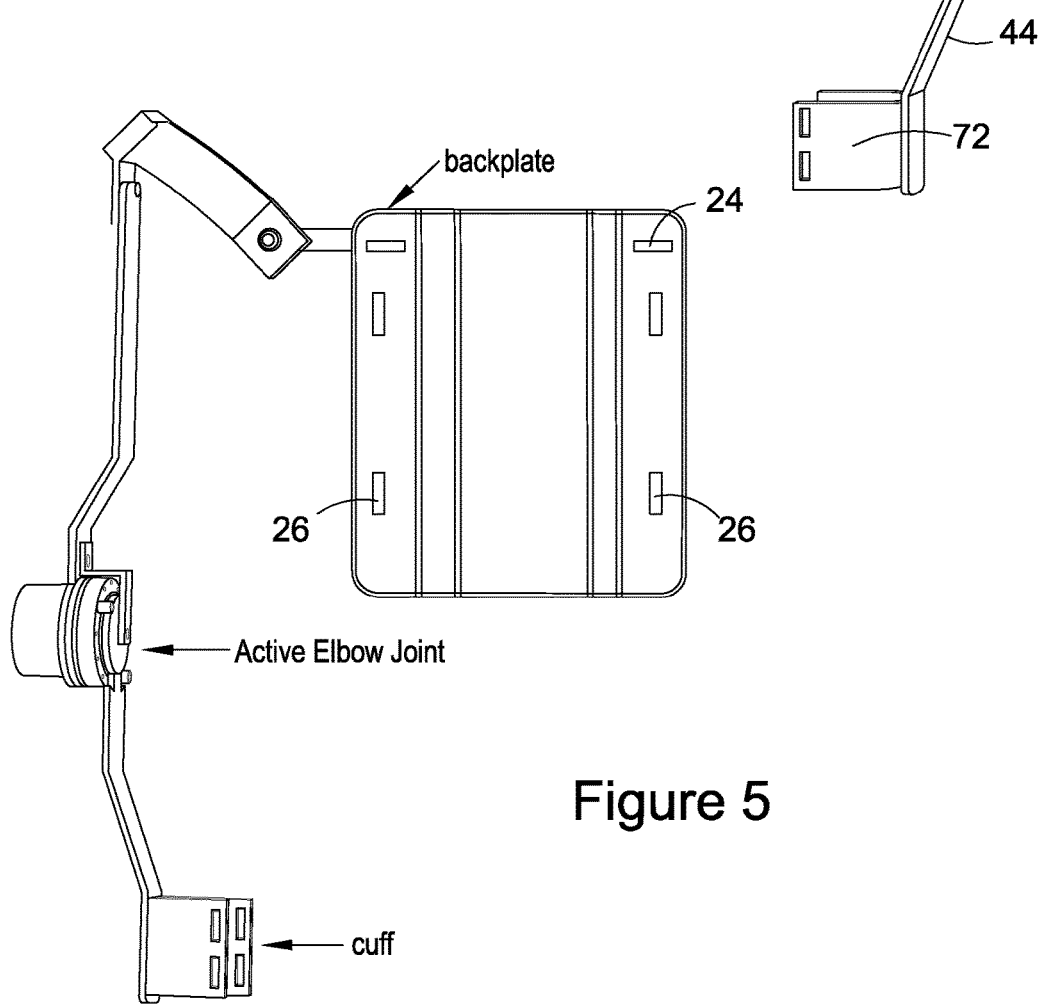
FIG. 5 shows a back perspective view of the wearable orthosis apparatus shown in FIG. 4.

As shown most clearly in FIG. 4 of the accompanying drawings, the linkage arrangement 14 of the apparatus 10 comprises a first linkage element in the form of shoulder rod 36, a second linkage element in the form of angled shoulder rod 38, a third linkage element in the form of shoulder link 40, a fourth linkage element in the form of upper arm member 42 and a fifth linkage element in the form of lower arm member 44.

The shoulder rod 36 is coupled to the back plate 18 by a coupler 46, such that the shoulder rod 36 extends vertically or substantially vertically relative to the user U.

More particularly, the shoulder rod 36 is rotatably coupled at a first end to the coupler 46 by a bearing 48 and at a second end to a coupler block 50 by a bearing 52, such that the shoulder rod 36 is rotatable about a vertical or substantially vertical axis AX1 relative to the user U as shown by arrow A in FIG. 4.

In use, rotation of the shoulder rod 36 relative to the axis AX1 provides a first degree of freedom of the apparatus 10.

The angled shoulder rod 38 is coupled to the coupler block 50, such that the angled shoulder rod 38 extends horizontally or substantially horizontally relative to the user U.

The angled shoulder rod 38 is rotatably coupled a first, proximal, end to the coupler block 50 by a bearing 54 and at a second, distal, end to the shoulder link 40 by a bearing 56, such that the angled shoulder rod 38 is rotatable about a horizontal or substantially horizontal axis AX2 relative to the user U as shown by arrow B in FIG. 4.

In use, rotation of the angled shoulder rod 38 relative to the coupler block 50 provides a second degree of freedom of the apparatus 10.

Shoulder link 40 is coupled at a first, proximal, end to the distal end of the angled shoulder rod 38 and at a second, distal, end to upper arm member 42.

As shown most clearly in FIGS. 2 and 3, shoulder link 40 is curved and, in use, extends in an anterior direction (towards the user's front) such that the distal end of the shoulder link 40 is disposed above, and rests on, the user's clavicle (collarbone). However, it will be recognised that the weight of the linkage arrangement 14 and the actuation arrangement 16 is substantially transferred to the support arrangement 12.

In the illustrated embodiment, the shoulder link 40 comprises a unitary component. The shoulder link 40 may be custom built to match the user's anthropometry.

Alternatively, the shoulder link 40 may be adjustable to match the user's anthropometry. For example, the shoulder link 40 may comprise a plurality of components coupled by a slider coupling or in a telescopic relationship.

The shoulder link 40 is configured to pivot about a third axis AX3 to provide a third degree of freedom of the apparatus 10, as shown by arrow C in FIG. 4.

The upper arm member 42 is coupled at a first, upper, end to the shoulder link 40 by a bearing 58 and at a second, lower, end to the actuator arrangement 16 of the apparatus 10. The upper arm member 42 is configured to pivot about a fourth axis AX4 to provide a fourth degree of freedom of the apparatus 10 as shown by arrow D in FIG. 4.

The lower arm member 44 is configured to pivot relative to the upper arm member 42 about a fifth axis AX5 defined by the actuation arrangement 16. In use, rotation of the lower arm member 44 about the fifth axis AX5 provides a fifth degree of freedom of movement of the apparatus 10 as shown by arrow E in FIG. 4.

Beneficially, the apparatus 10 is thus capable of five degrees of freedom of movement.

As shown in FIGS. 2 and 3, the upper arm member 42 is adjustable to match the user's anthropometry, comprising a first upper arm element 60 and a second upper arm element 62 coupled together by a slider coupling 64. The first upper arm element 60 and the second upper arm element 62 may alternatively be arranged in a telescopic relationship. Alternatively, the upper arm member 42 may comprise a unitary component. The upper arm member 42 may be custom built to match the user's anthropometry, such as by additive manufacture or other suitable method of manufacture.

The lower arm member 44 is coupled at a first, upper, end to the actuator arrangement of the apparatus 10.

The lower arm member 44 is adjustable to match the user's anthropometry, comprising a first lower arm element 66 and a second lower arm element 68 coupled together by a slider coupling 70. The first lower arm element 66 and the second lower arm element 68 may alternatively be arranged in a telescopic relationship. Alternatively, the lower arm member 44 may comprise a unitary component. The lower arm member 44 may be custom built to match the user's anthropometry, such as by additive manufacture or other suitable method of manufacture.

A cuff 72 is coupled to, or forms part of, the lower arm member 44, the cuff 72 configured for coupling the apparatus 10 to the user's lower arm. An adjustable strap 73 is used to secure the user's lower arm to the cuff 72.

The user input signal may be generated by a sensor arrangement comprising a sensor S embedded, coupled to or otherwise disposed on the cuff 72. In the illustrated embodiment, the sensor S comprises an accelerometer.

In use, force generated by the actuator arrangement 16 is transferred to the user's arm A through the cuff 72.

As described above, the actuation arrangement 16 of the apparatus 10 is configured to operate the linkage arrangement 14 of the apparatus 10.

Figure 6:
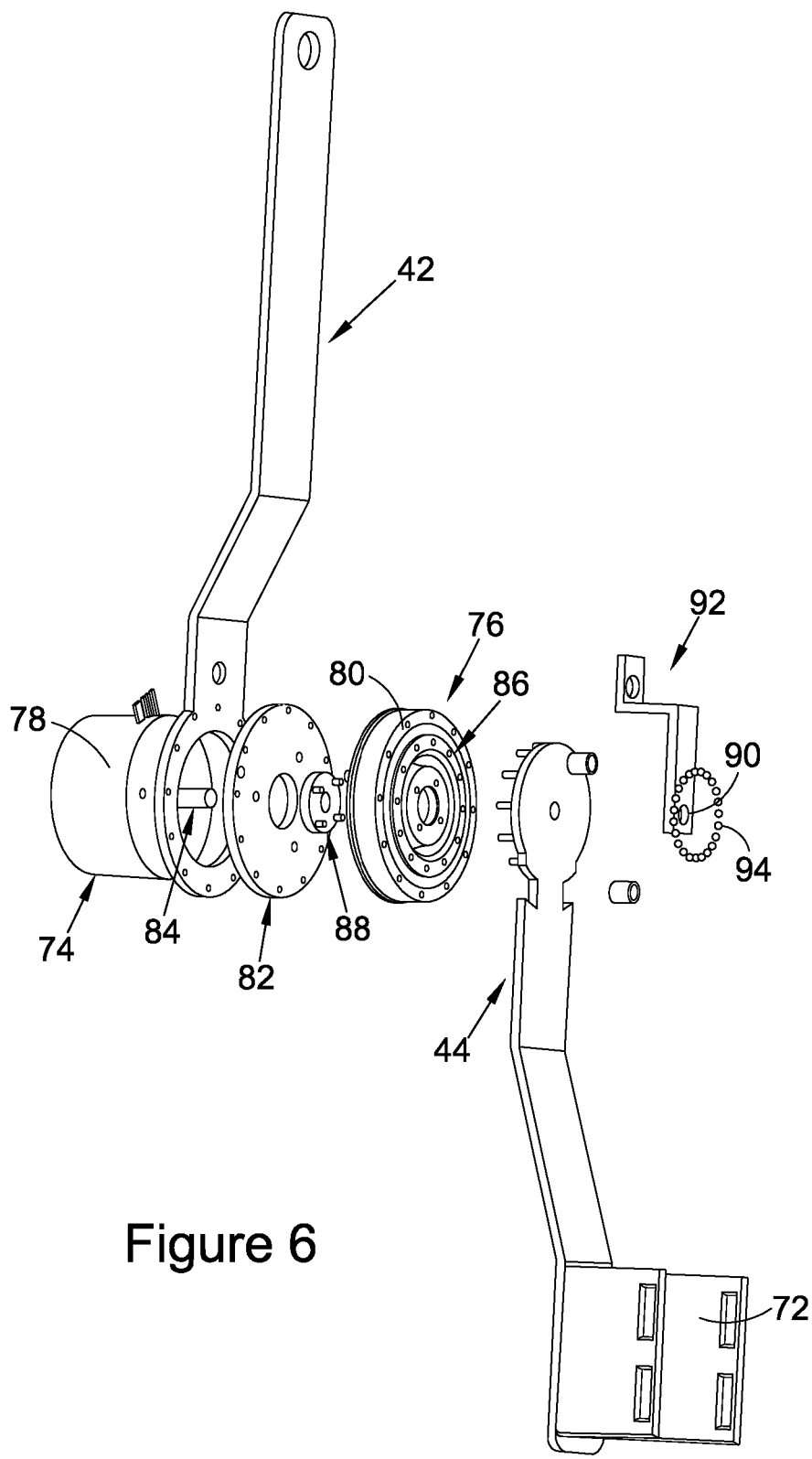
FIG. 6 shows an exploded view of the actuation arrangement of the apparatus shown in FIGS. 1 to 5.

FIG. 6 of the accompanying drawings shows an exploded view of the actuation arrangement 16 of the apparatus 10.

As shown in FIG. 6, the actuation arrangement 16 comprises a rotary drive in the form of a motor 74. In the illustrated embodiment, the rotary drive takes the form of a brushless DC electric motor (BLDC motor). Beneficially, the use of a BLDC motor provides a high power-to-weight ratio while also providing a sufficiently fast response time to meet the user need for responsiveness.

The actuation arrangement 16 further comprises a gear arrangement which in the illustrated embodiment takes the form of a strain wave gear drive 76, and more particularly a harmonic Drive®. The strain wave gear drive 76 is interposed between the motor 74 and the lower arm member 44.

In the illustrated embodiment, the strain wave gear drive 76 has a gear reduction ratio of 1:100. Beneficially, the provision of a strain wave gear drive 76 provides a gear drive which is compact, has low backlash, high gear reduction ratio and low weight for the given gear ratio.

Housing 78 of motor 74 and the non-moving circular spline 80 of the strain wave gear drive 76 are fixed to the upper arm member 42 via an attachment plate 82 while the shaft 84 of the motor 74 is coupled to the output shaft—flex spline 86—of the strain wave gear drive 76 via a coupler 88.

A magnetic rotary encoder 90 is incorporated into a housing 92 and is configured to measure the position of the lower arm member 44 relative to the upper arm member 42. A cylindrical magnet 94 is embedded in or otherwise disposed on the lower arm member 44 for measuring its orientation by the rotary encoder 90. In the illustrated embodiment, the rotary encoder 90 takes the form of an RM08 rotary magnetic encoder. Beneficially, the magnetic rotary encoder 90 provides high accuracy and low footprint.

To control the position of the flexspline output shaft of the strain wave gear drive 76, the apparatus 10 further comprises or is operatively associated with a position controller 96. In the illustrated embodiment, the position controller 96 takes the form of a software based PID (Proportional Integral Derivative) position controller.

Figure 7:
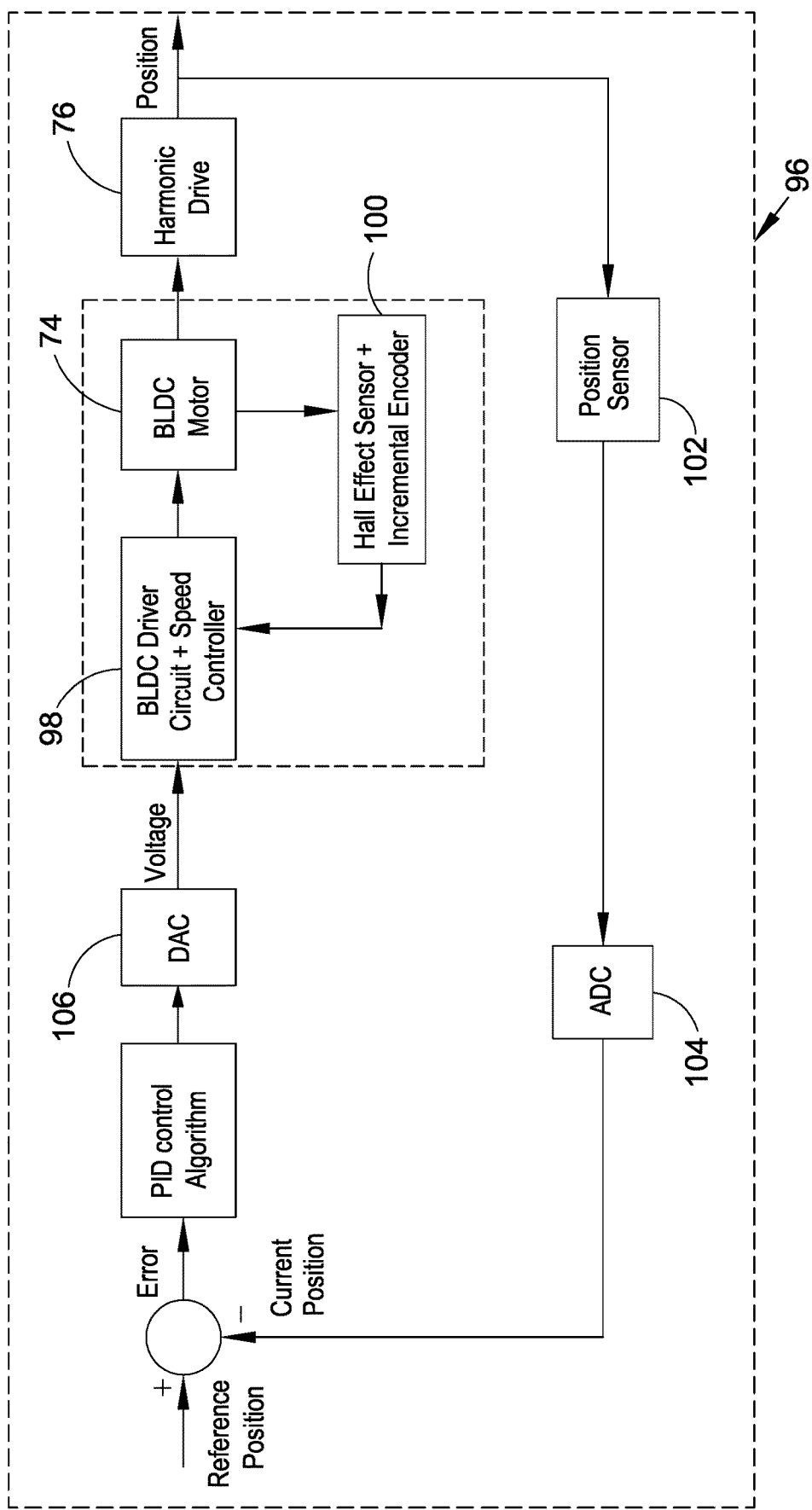
FIG. 7 shows a block diagram of a position controller of the apparatus shown in FIG. 1.

FIG. 7 shows a block diagram of the position controller 96 of the apparatus 10.

As described above, the apparatus 10 uses a harmonic Drive® to increase the torque and to reduce the rotational speed of the motor 74. The BLDC motor used in the illustrated embodiment is controlled using a ESCON 70/10Maxon motor controller 98 comprising the driver circuits and control system needed to control the speed of the motor 74. The motor uses Hall effect sensors and an incremental encoder (together represented by reference 100) as feedback to the ESCON speed controller 98.

Feedback from two sensors 102 will increase the positional accuracy of the output shaft 84 of the motor 74.

A digital PID controller has been implemented in a 32-bitARM microcontroller (MCU). This controller consists of anti-windup, and output saturation limit features. It also consists of a derivative filter to reduce noise. The MCU consists of a 12-bit analogue to digital converter (ADC) 104 and a 10-bit digital-to-analogue converter (DAC) 106 for communicating with external devices. The output from the magnetic encoder 92 is an analogue voltage, which is digitised by the ADC 104 in the MCU and then converted into degrees based on a calibration curve. The output of the PID controller 98 is then given to the ESCON controller via the DACport 106 in the MCU. The control algorithm is implemented in a timer interrupt to run at a sampling frequency of 1000 Hz.

The position controller 96 operates as a cascading control system consisting of an inner and outer control loop. The inner loop implemented in the ESCON board corresponds to a motor speed controller that maintains the required speed of the BLDC motor 74. The outer loop monitors the current shaft position of the strain wave gear drive 76.

Based on the differences between the reference position and current position, the PID controller 96 generates a corresponding voltage which is sent as an input to the speed controller via the DACport 106 in the MCU. On receiving the input from the DAC 106, the speed controller controls the speed and direction of the motor's 74 rotation.

When there is no error between the reference position and feedback position, the output from the PID controller 96 becomes zero and thus brings the motor 74 to an idle position.

The objective of the PID algorithm in position control is to maintain a given position according to a set point at any given time and to be able to reach new set point without causing any instability in the system.

Beneficially, the position controller 88 according to embodiments of the present invention provides for the safe operation of the apparatus 10 as it ensures that elbow joint of the apparatus 10 will not operate beyond the range of natural range of motion of the human elbow (i.e., 0 to 130 degrees).

Moreover, position controller 96 can be used with other control strategies such as admittance method or with Electromyographic (EMG) signals.

Since the controller 96 utilises a cascading control system, inner speed control loop needs to be tuned first. Inner loop tuning is performed using software supplied by Maxon Motor (ESCONStudio). Prior to the tuning process, different parameters of the motor 74 is set such as the nominal current, voltage, speed, etc. The response of the motor 74 corresponding to an input voltage of the controller 96 is set in the software. The speed of the motor 74 is limited to 1000 rpm. The speed of the motor 74 linearly varies from −1000 rpm to 1000 rpm to an input from 0V to 3V. Hence, a minimum voltage of 1.5V is required to maintain a speed of 0 rpm. After setting the parameters and desired behaviour, an automatic tuning of the inner loop is performed through the software.

After tuning the inner speed control loop, the cascading position control loop is then tuned. A manual tuning approach is chosen to stabilise the position controller 88. The parameters, proportional gain (Kp), integral gain (Ki) and derivative gain (Kd), determines the stability, steady state error, overshoot, settling time and rise time of the system response. During the tuning process, PID gains are changed iteratively until it meets the required performance goals of the system.

Beneficially, manual tuning does not require a mathematical model of the system, which is difficult to achieve in physical system. However, following a structured tuning process will help to stabilise the control loop without taking considerable time.

Figure 8:
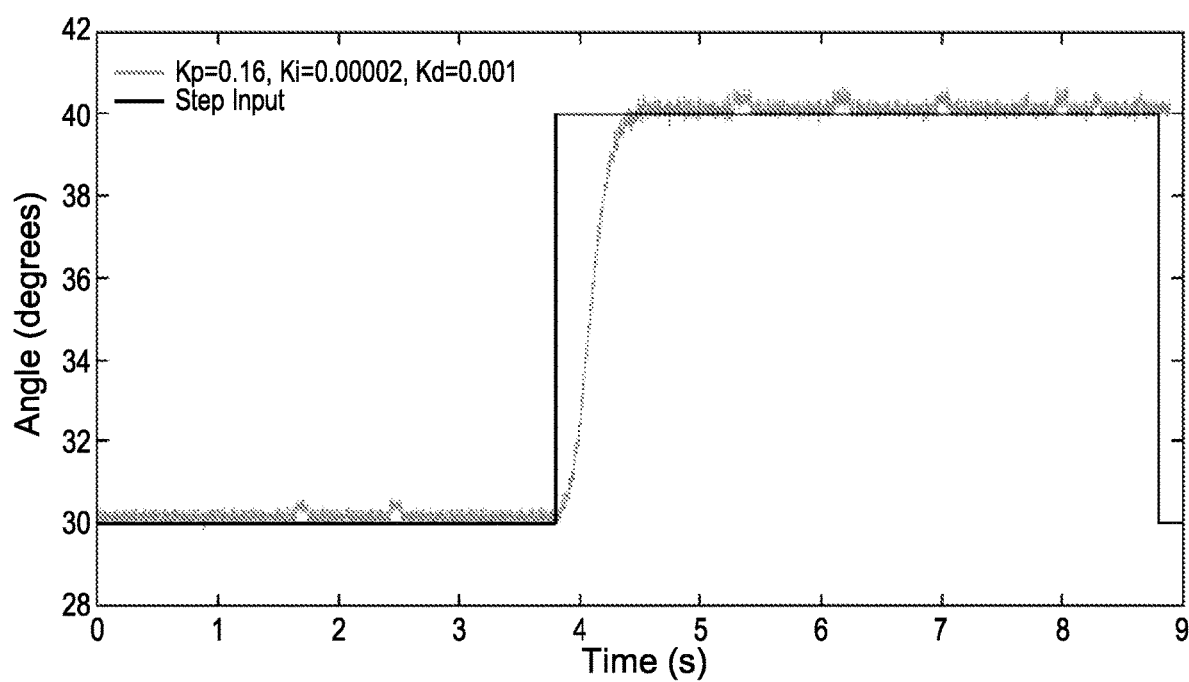
FIG. 8 shows a step response of the system to different PID gains.

FIG. 8 shows a step response of the system to different PID gains. As shown in FIG. 8, after tuning the control loop, the system response is well within the limits of the desired behaviour. A good position controller should not have overshoot, undershoot and steady state error. Moreover, settling time of the response should be less. The response of the system shows that it does not have any overshoot or undershoot and also it has a good settling time. However, the output contains some random noise. A good filter should be needed to avoid noise in the PID loop. The PID gains with Kp=0.16, Ki=0.00002 and Kd=0.001 gives the best response for the system.

It will be apparent to those of skill in the art that the above-described embodiments are merely exemplary of the present invention and that various modifications and improvements may be made thereto without departing from the scope of the invention.

For example, FIGS. 9 to 14 show an apparatus 10' according to a second embodiment of the present invention. The apparatus 10' is similar to the apparatus and like components are represented by like numerals.

Figure 9:
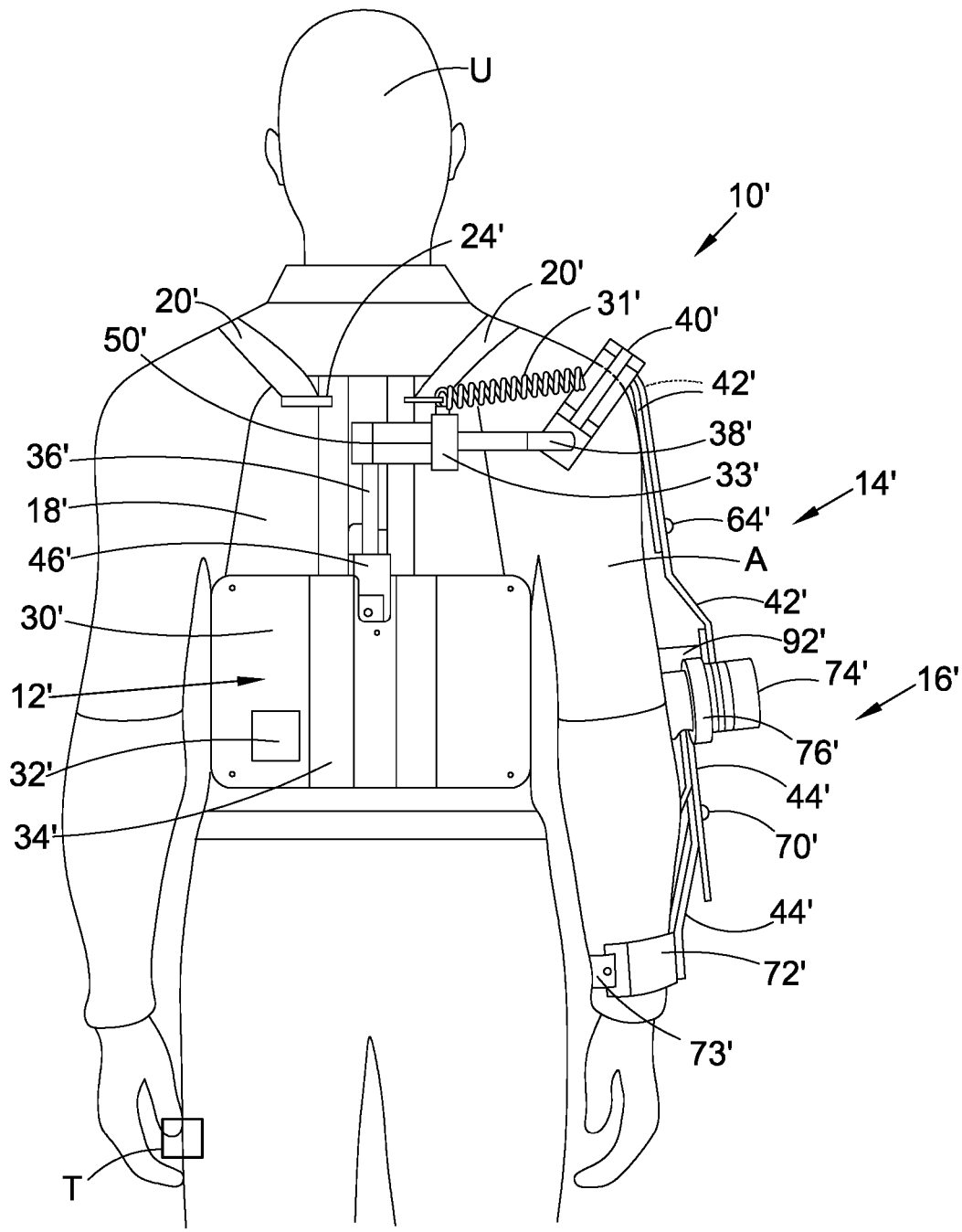
FIGS. 9 to 14 show a wearable orthosis apparatus according to a second embodiment of the present invention.

As shown in FIG. 9, the apparatus 10' comprises a support arrangement 12' for supporting the apparatus 10' on the user U, a linkage arrangement 14' coupled to the support arrangement 12' and for coupling to an arm A of the user U, and an actuation arrangement 16' for operating the linkage arrangement 14' and thereby manipulating the user's arm A in response to a user input signal.

Figure 10:
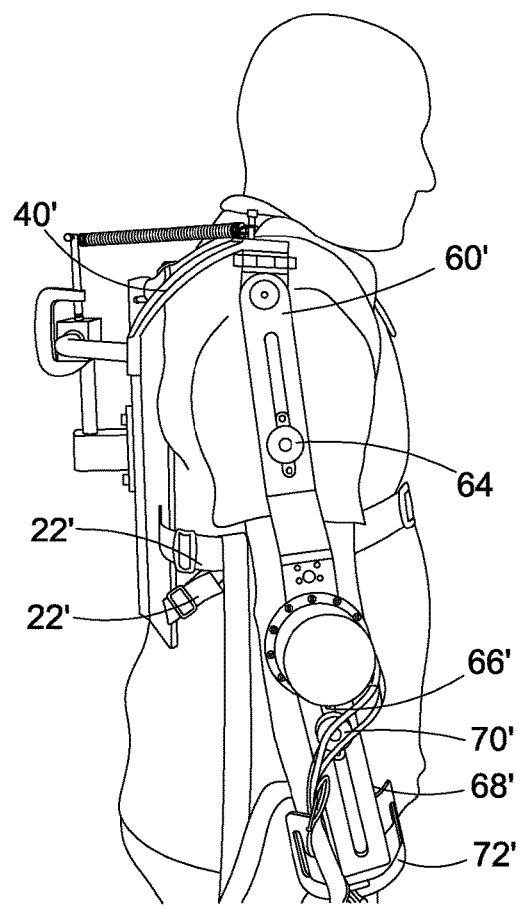
Figure 11:
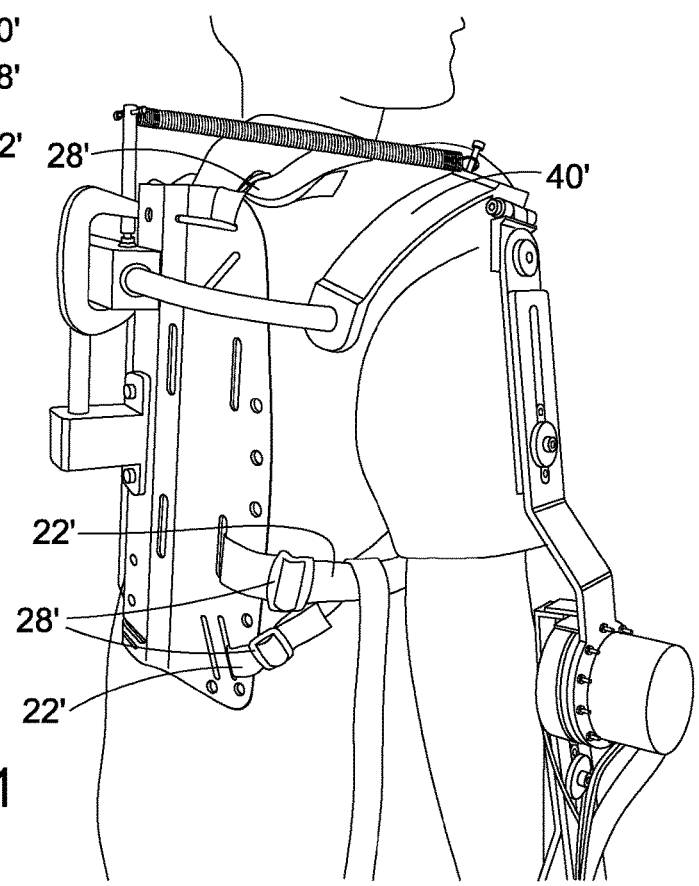

In the illustrated embodiment, the support arrangement 12' comprises a back plate 18', shoulder straps 20', and waist straps 22' (shown most clearly in FIGS. 10 and 11). The shoulder straps 20' and waist straps 22' extend through slots 24', 26' in the back plate 18' and comprise slide adjusters 28' or other suitable adjusters, to permit the support arrangement 12' to be adapted to the user's U anthropometry.

While in the illustrated embodiment, shoulder straps 20' and waist straps 22' are provided, it will be recognised that the support arrangement 12' may take a number of different forms. For example, some embodiments may be provided without waist straps. At least part of the support arrangement 12' may alternatively be integrally formed with a garment, such as a jacket, suitable for being worn by the user U.

An electronics enclosure 30' is disposed on the back plate 18'. The electronics enclosure 30' houses a controller 32' for the apparatus 10. An onboard power supply in the form of a battery pack 34 is disposed in the electronics enclosure 30'.

The back plate 18' supports the mass of the linkage arrangement 14' and the actuation arrangement 16'.

One or more spring element or other resilient element 31' may be provided to stabilise free movement of the shoulder joint assembly. In the illustrated embodiment, the spring element 31' is attached via spring attachment 33'.

Users with reduced or no feeling in their arm are known to be adversely affected by balance issues due at least in part to the lack of feedback from the affected arm, balance issues which can be exacerbated by any unbalanced load on one side of the user's body. Beneficially, the back plate 18' distributes the weight of the apparatus 10' across the back of the user U, such that the user U will not feel weight a significant unbalanced load on one side of their body due to the asymmetric location of the apparatus 10' on one arm.

In the illustrated embodiment, the back plate 18' is constructed from a carbon fibre composite material, providing a back plate 18' which is lightweight while being strong enough to carry the mass of the linkage arrangement 14', the actuation arrangement 16', the electronics enclosure 30' and the battery pack 34'.

As described above, the back plate 18' provides mounting for the linkage arrangement 14'.

Figure 12:
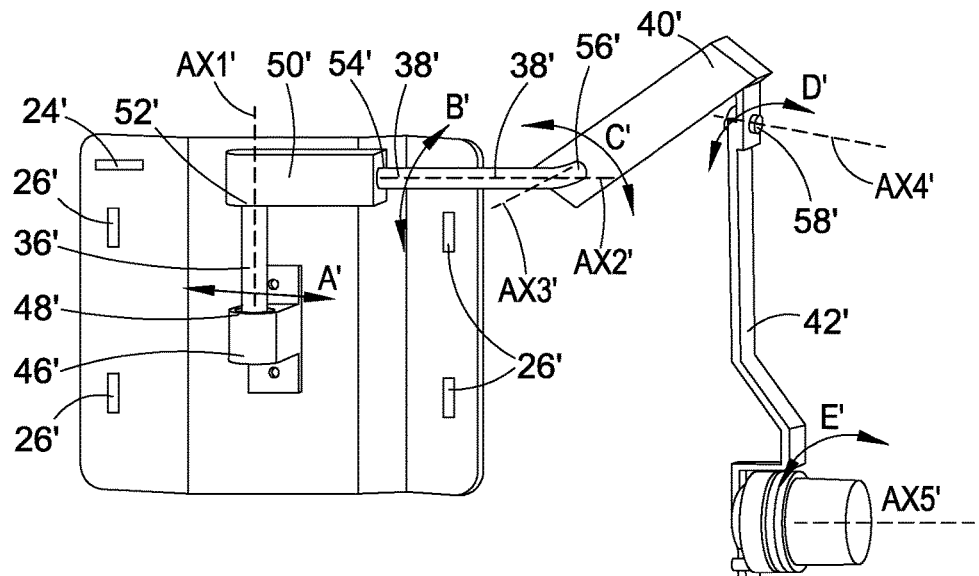
Figure 13:
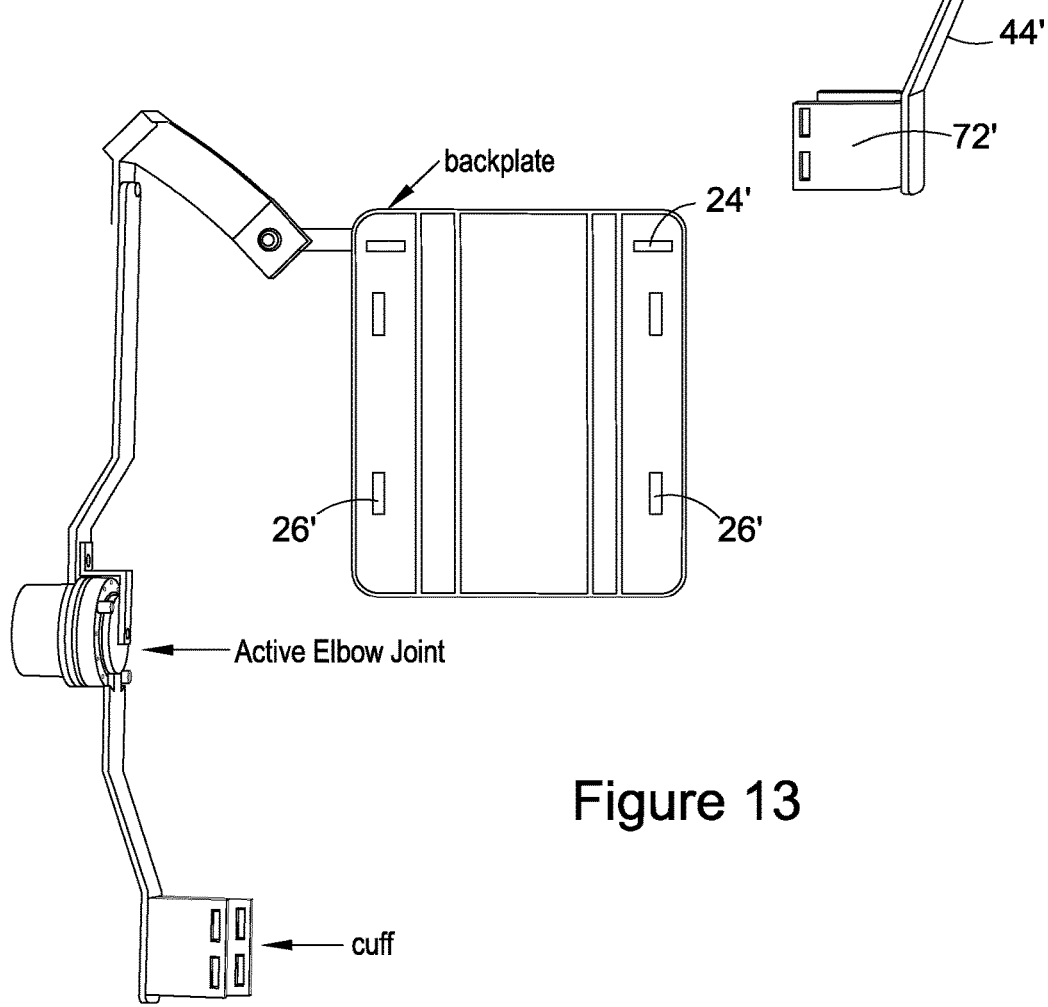
Figure 14:
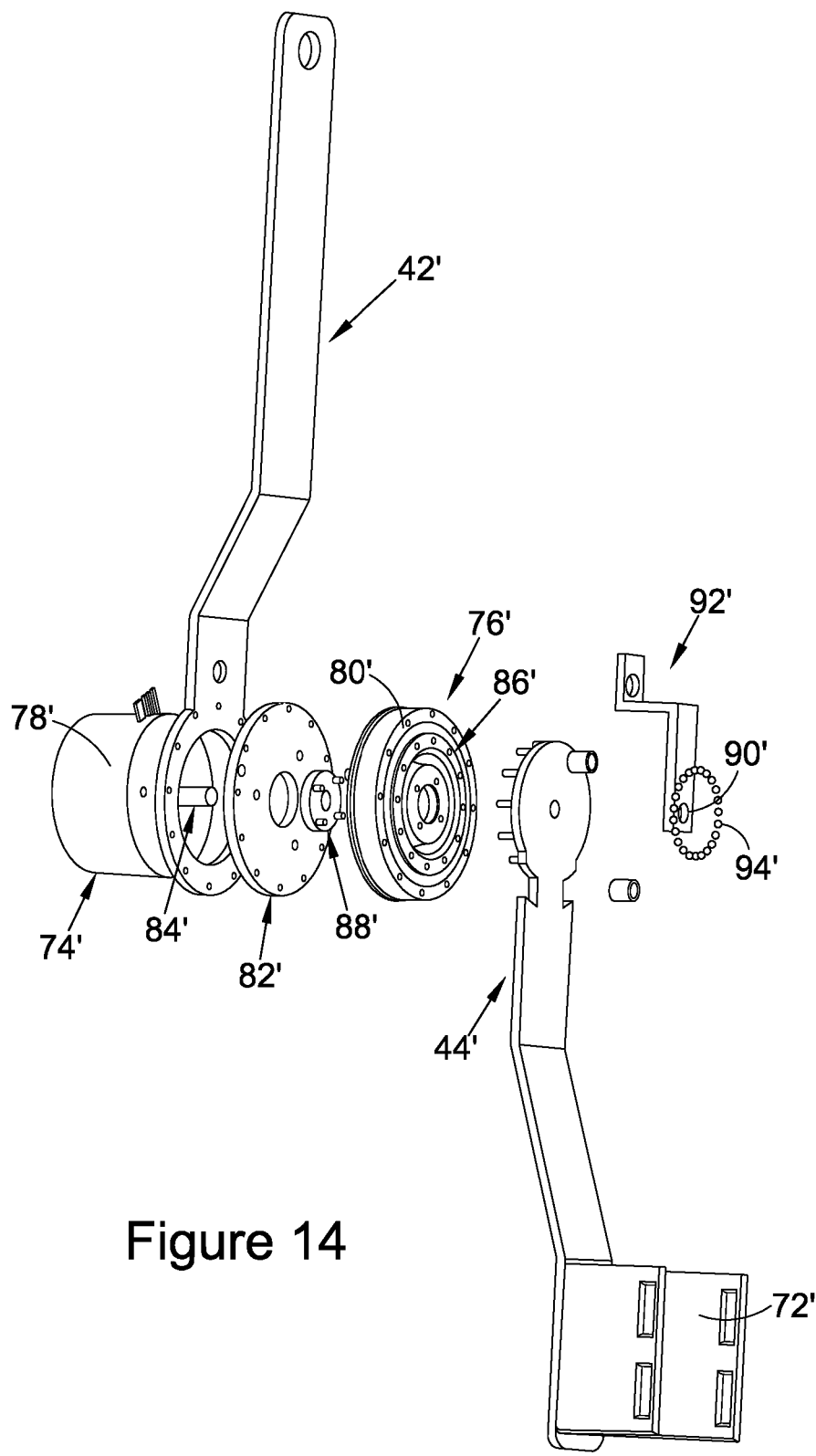

As shown most clearly in FIG. 12 of the accompanying drawings, the linkage arrangement 14' of the apparatus 10' comprises a first linkage element in the form of shoulder rod 36', a second linkage element in the form of angled shoulder rod 38', a third linkage element in the form of shoulder link 40, a fourth linkage element in the form of upper arm member 42' and a fifth linkage element in the form of lower arm member 44.

As will be described further below, the apparatus 10' is capable of five degrees of freedom of movement, the shoulder rod 36', angled shoulder rod 38' and shoulder link 40' providing three degrees of freedom of movement while upper arm member 36' and lower arm member 38 provide two degrees of freedom of movement.

The shoulder rod 36' is coupled to the back plate 18' by a coupler 46', such that the shoulder rod 36' extends vertically or substantially vertically relative to the user U.

More particularly, the shoulder rod 36' is rotatably coupled at a first end to the coupler 46' by a bearing 48' and at a second end to a coupler block 50' by a bearing 52', such that the shoulder rod 36' is rotatable about a vertical or substantially vertical axis AX1' relative to the user U as shown by arrow A' in FIG. 12.

In use, rotation of the shoulder rod 36' relative to the axis AX1 provides a first degree of freedom of the apparatus 10'.

The angled shoulder rod 38' is coupled to the coupler block 50', such that the angled shoulder rod 38' extends horizontally or substantially horizontally relative to the user U.

The angled shoulder rod 38' is rotatably coupled a first, proximal, end to the coupler block 50' by a bearing 54' and at a second, distal, end to the shoulder link 40 by a bearing 56', such that the angled shoulder rod 38' is rotatable about a horizontal or substantially horizontal axis AX2' relative to the user U as shown by arrow B' in FIG. 12.

In use, rotation of the angled shoulder rod 38' relative to the coupler block 50' provides a second degree of freedom of the apparatus 10'.

Shoulder link 40' is coupled at a first, proximal, end to the distal end of the angled shoulder rod 38' and at a second, distal, end to upper arm member 42'.

As shown most clearly in FIGS. 10 and 11, shoulder link 40' is curved and, in use, extends in an anterior direction (towards the user's front) such that the distal end of the shoulder link 40' is disposed above, and rests on, the user's clavicle (collarbone). However, it will be recognised that the weight of the linkage arrangement 14' and the actuation arrangement 16 is substantially transferred to the support arrangement 12'.

In the illustrated embodiment, the shoulder link 40' comprises a unitary component. The shoulder link 40' may be custom built to match the user's anthropometry.

Alternatively, the shoulder link 40' may be adjustable to match the user's anthropometry. For example, the shoulder link 40' may comprise a plurality of components coupled by a slider coupling or in a telescopic relationship.

The shoulder link 40' is configured to pivot about a third axis AX3' to provide a third degree of freedom of the apparatus 10', as shown by arrow C' in FIG. 12.

The upper arm member 42' is coupled at a first, upper, end to the shoulder link 40' by a bearing 58' and at a second, lower, end to the actuator arrangement 16 of the apparatus 10'. The upper arm member 42' is configured to pivot about a fourth axis AX4' to provide a fourth degree of freedom of the apparatus as shown by arrow D' in FIG. 12.

The lower arm member 44' is configured to pivot relative to the upper arm member 42' about a fifth axis AX5' defined by the actuation arrangement 16'. In use, rotation of the lower arm member 44' about the fifth axis AX5' provides a fifth degree of freedom of movement of the apparatus 10' as shown by arrow E' in FIG. 10.

Beneficially, the apparatus 10' is thus capable of five degrees of freedom of movement.

As shown in FIGS. 10 and 11, the upper arm member 42' is adjustable to match the user's anthropometry, comprising a first upper arm element 60' and a second upper arm element 62' coupled together by a slider coupling 64'. The first upper arm element 60' and the second upper arm element 62' may alternatively be arranged in a telescopic relationship. Alternatively, the upper arm member 42' may comprise a unitary component. The upper arm member 42' may be custom built to match the user's anthropometry, such as by additive manufacture or other suitable method of manufacture.

The lower arm member 38' is coupled at a first, upper, end to the actuator arrangement of the apparatus 10'.

The lower arm member 44' is adjustable to match the user's anthropometry, comprising a first lower arm element 66' and a second lower arm element 68' coupled together by a slider coupling 70'. The first lower arm element 66' and the second lower arm element 68' may alternatively be arranged in a telescopic relationship. Alternatively, the lower arm member 44' may comprise a unitary component. The lower arm member 44' may be custom built to match the user's anthropometry, such as by additive manufacture or other suitable method of manufacture.

A cuff 72' is coupled to, or forms part of, the lower arm member 44', the cuff 72' configured for coupling the apparatus 10' to the user's lower arm. An adjustable strap 73' is used to secure the user's lower arm to the cuff 72

Whereas in the apparatus 10, the user input signal is provided by a sensor S provided in the cuff 72, in the apparatus 10' the user input signal is provided by a user operated trigger switch T.

The invention claimed is:

1. A wearable single-arm orthosis apparatus for use in the rehabilitation, assistance and/or augmentation of arm strength in a user, comprising:
   a support arrangement for supporting the apparatus on the user, such that the apparatus can be carried by the user;
   a linkage arrangement coupled to the support arrangement and configured for coupling to an arm of a user; and
   an actuator arrangement coupled to the linkage arrangement and configured to move the linkage arrangement and thereby manipulate the user's arm in response to a user input signal,
   wherein the support arrangement comprises a back plate supporting the mass of the linkage arrangement and the actuator arrangement, and
   wherein the linkage arrangement comprises:
   a first linkage element coupled to the back plate such that the first linkage element extends vertically or substantially vertically relative to the user, the first linkage element being rotatable about a vertical or substantially vertical axis relative to the user so as to provide a first degree of freedom of the apparatus;
   a second linkage element rotatable about a horizontal or substantially horizontal axis relative to the user so as to provide a second degree of freedom of the apparatus;
   a third linkage element configured to pivot about a third axis to provide a third degree of freedom of the apparatus;
   a fourth linkage element in the form of an upper arm member, the fourth linkage element configured to pivot about a fourth axis to provide a fourth degree of freedom of the apparatus; and
   a fifth linkage element in the form of a lower arm member, the fifth linkage element configured to pivot about a fifth axis defined by the actuator arrangement to provide a fifth degree of freedom of the apparatus.

2. The apparatus of claim 1, wherein the actuator arrangement comprises a sensor arrangement comprising a sensor configured to sense the user input signal applied to the apparatus by the user.

3. The apparatus of claim 2, wherein the user input signal comprises a pressure force applied to the linkage arrangement of the wearable orthosis apparatus.

4. The apparatus of claim 1, wherein the actuator arrangement comprises a controller configured to actuate the actuator arrangement of the apparatus in response to the user input signal to operate the linkage arrangement, and thereby manipulate the user's arm in response to the user input signal.

5. The apparatus of claim 1, wherein the actuator arrangement comprises a trigger switch configured for operation by the user.

6. The apparatus of claim 1, wherein the support arrangement comprises at least one strap.

7. The apparatus of claim 1, wherein the linkage arrangement comprises a shoulder joint assembly configured to provide three degrees of freedom of movement.

8. The apparatus of claim 7, wherein the shoulder joint assembly is passive.

9. The apparatus of claim 1, wherein the linkage arrangement comprises an arm assembly configured to provide two degrees of freedom of movement.

10. The apparatus of claim 9, wherein an elbow joint defined by the arm assembly is active.

11. The apparatus of claim 7, comprising one or more resilient element configured to stabilise free movement of the shoulder joint assembly.

12. The apparatus of claim 1, comprising a cuff configured for coupling the apparatus to the user's lower arm such that a force generated by the actuator arrangement is transferred to the user's arm through the cuff.

13. The apparatus of claim 12, wherein at least part of the sensor arrangement is disposed in, or mounted on, the cuff.

14. The apparatus of claim 1, wherein the actuator arrangement comprises a rotary drive.

15. The apparatus of claim 14, wherein the rotary drive comprises a brushless DC electric motor.

16. The apparatus of claim 14, wherein the actuator arrangement comprises a gear arrangement interposed between the rotary drive and the linkage arrangement.

17. The apparatus of claim 16, wherein at least one of:
the gear arrangement comprises a strain wave gear drive;
the apparatus comprises or is operatively associated with a position controller configured to control the position of an output shaft of the gear arrangement;
the apparatus comprises or is operatively associated with a position controller configured to control the position of an output shaft of the gear arrangement, the position controller comprising a software-based PID (Proportional Integral Derivative) position controller.

18. Use of the apparatus of claim 1 to rehabilitate, assist, and/or augment arm strength in a user.

19. The apparatus of claim 1, wherein at least one of:
the first linkage element is coupled to the back plate by a coupler, the first linkage element rotatably coupled at a first end to the coupler and at a second end to a coupler block;
the second linkage element is rotatably coupled at a first, proximal, end to the coupler block and at a second, distal, end to the third linkage element; and/or
the third linkage element is coupled at a first, proximal, end to the distal end of the second linkage element and at a second, distal, end to the fourth linkage element;
the fourth linkage element is coupled at a first, upper, end to the third linkage element and at a second, lower, end to the actuator arrangement of the apparatus; and
the fifth linkage element is coupled at a first, upper, end to the actuator arrangement of the apparatus.

* * * * *